(12) United States Patent
Sévigny et al.

(10) Patent No.: US 6,291,175 B1
(45) Date of Patent: Sep. 18, 2001

(54) METHODS FOR TREATING A NEUROLOGICAL DISEASE BY DETERMINING BCHE GENOTYPE

(75) Inventors: Pierre Sévigny; Keith Schappert, both of Montreal (CA); Heiko Wiebusch, Münster (DE); Philippe Amouye, Lille (FR)

(73) Assignees: Variagenics, Inc., Cambridge, MA (US); Institut Pasteur de Lille, Lille (FR)

( * ) Notice: Subject to any disclaimer, the term of this patent is extended or adjusted under 35 U.S.C. 154(b) by 0 days.

(21) Appl. No.: 09/334,489

(22) Filed: Jun. 16, 1999

Related U.S. Application Data
(60) Provisional application No. 60/089,406, filed on Jun. 16, 1998.

(51) Int. Cl.[7] .............................. C12Q 1/68; C07H 21/04; A61K 49/00; A01N 37/18
(52) U.S. Cl. ................... 435/6; 536/23.1; 514/2; 424/9.2
(58) Field of Search ................ 435/6; 536/23.1; 424/9.2; 514/2

(56) References Cited

FOREIGN PATENT DOCUMENTS

| | | |
|---|---|---|
| WO 96/21744 | 7/1996 | (WO) . |
| WO 98/27226 | 6/1998 | (WO) . |
| WO 98/27227 | 6/1998 | (WO) . |
| WO 99/14367 | 3/1999 | (WO) . |

OTHER PUBLICATIONS

Erlich et al. "Population diversity and distinct haplotype frequencies associated with ACHE and BCHE genes" Genomics, vol. 22, p. 288–295, 1994.*

Brindle et al., "Analysis of the butyrylcholinesterase Gene and Nearby Chromosome 3 Markers in Alzheimer Disease," Hum. Mol. Genet. 7:933–935 (1998).

Lehmann et al., "Synergy Between the Genes for Butyrylcholinesterase K Variant and Apolipoprotein E4 in Late–Onset Confirmed Alzheimer's Disease," Hum. Mol. Genet. 6:1933–1936 (1997).

Main et al., "Apolipoprotein E Genotyping Using the Polymerase Chain Reaction and Allele–Specific Oligonucleotide Primers," J. Lipid. Res. 32:183–187 (1991).

Richard et al., "APOE Genotyping and Response to Drug Treatment in Alzheimer's Disease," Lancet 349:539 (1997).

Singleton et al., "No Association Between the K Variant of the Butyrylcholinesterase Gene and Pathologically Confirmed Alzheimer's Disease," Hum. Mol. Genet. 7:937–939 (1998).

La Du et al., "Phenotypic and Molecular Biological Analysis of Human Butyrylcholinesterase Variants," Clin. Biochem. 23:423–431 (1990).

Ki et al "No Association between the genes for BCHE–K variant and apoE4 in Late–onset Alzheimer's disease" Am. J. of Medical Genetics, vol 88, No. 2, p. 113–115, Apr. 1999.*

Hiltunen et al "BCHE–K vairnat and apoE4 genes do no act in synergy in Finnish late–onset Alzheimer's disease patients" Neuroscience Letters, vol 250, No. 1, p. 69–71, Jun. 1988.*

Crawford et al "The BCHE gene is neither indepentdently nor synergistically associated with the late–onset AD in clinical and community–based populations" Neuroscience Letters, vol 249, No. 2–3, p. 115–118, Jun. 1998.*

Soreq et al "Mutations in the impared expression in the ACHE and BCHE genes: neurological implications" Biomed and Pharmacother, vol 48, No. 5–6, p. 253–259, 1994.*

Camps et al "Synthesis, in vistro pharmacology, and molecular modeling of very potent tacrine" J. Med. Chem, vol 42, No. 17, pp. 3227–3242, Aug. 1999.*

McKenna et al "Novel tacrine analogues for potential use against Alzheimer's Disease" J. Med, Chem. vol 40, No. 22, p. 3516–3523, Oct. 1997.*

Wang et al "Effects of bis(7)–tacrine, a novel anti–Alzheimer's agent, on rat brain ACHe" Neuropharmacology, vol 10, No. 4, pp. 789–793, Mar. 1999.*

Lowenstein–Lichtenstein Y. et al., "Genetic predisposition to adverse consequences of anti–cholinesterase 'atipical' BCHE carriers," Nature Medicine 1(10):1082–1085 (1995).

Ehrlich G. et al., Population diversity of point mutations in the human ACHE and BCHE genes predicts variable responses to anticholinesterase drugs, Adv. Behav. Biology 44:661–667 (1995).

* cited by examiner

*Primary Examiner*—W. Gary Jones
*Assistant Examiner*—Jeanine Goldberg
(74) *Attorney, Agent, or Firm*—Clark & Elbing LLP; Kristina Bieker-Brady

(57) ABSTRACT

Disclosed herein is a method for treating a patient with a neurological disease by determining a patient's BCHE allele status.

8 Claims, 5 Drawing Sheets

BCHE cDNA sequence (SEQ ID NO:1)

```
   1 tactgaatgt cagtgcagtc caatttacag gctggagcag cagctgcatc ctgcatttcc
  61 ccgaagtatt acatgatttt cactccttgc aaactttacc atctttgttg cagagaatcg
 121 gaaatcaata tgcatagcaa agtcacaatc atatgcatca gatttctctt ttggtttctt
 181 ttgctctgca tgcttattgg gaagtcacat actgaagatg acatcataat tgcaacaaag
 241 aatggaaaag tcagagggat gaacttgaca gttttggtg gcacggtaac agcctttctt
 301 ggaattccct atgcacagcc acctcttggt agacttcgat tcaaaaagcc acagtctctg
 361 accaagtggt ctgatatttg gaatgccaca aaatatgcaa attcttgctg tcagaacata
 421 gatcaaagtt ttccaggctt ccatggatca gagatgtgga cccaaacac tgacctcagt
 481 gaagactgtt tatatctaaa tgtatggatt ccagcaccta aaccaaaaaa tgccactgta
 541 ttgatatgga tttatggtgg tggttttcaa actggaacat catctttaca tgtttatgat
 601 ggcaagtttc tggctcgggt tgaaagagtt attgtagtgt caatgaacta tagggtgggt
 661 gccctaggat tcttagcttt gccaggaaat cctgaggctc agggaacat gggtttattt
 721 gatcaacagt tggctcttca gtgggttcaa aaaaatatag cagcctttgg tggaaatcct
 781 aaaagtgtaa ctctctttgg agaaagtgca ggagcagctt cagttagcct gcatttgctt
 841 tctcctggaa gccattcatt gttcaccaga gccattctgc aaagtggatc ctttaatgct
 901 ccttgggcgg taacatctct ttatgaagct aggaacagaa cgttgaactt agctaaattg
 961 actggttgct ctagagagaa tgagactgaa ataatcaagt gtcttagaaa taaagatccc
1021 caagaaattc ttctgaatga agcatttgtt gtcccctatg ggactccttt gtcagtaaac
1081 tttggtccga ccgtggatgg tgattttctc actgacatgc agacatatt acttgaactt
1141 ggacaattta aaaaaaccca gattttggtg ggtgttaata agatgaagg gacagctttt
1201 ttagtctatg gtgctcctgg cttcagcaaa gataacaata gtatcataac tagaaaagaa
1261 tttcaggaag gtttaaaaat attttttcca ggagtgagtg agtttggaaa ggaatccatc
1321 cttttcatt acacagactg ggtagatgat cagagacctg aaaactaccg tgaggccttg
1381 ggtgatgttg ttggggatta aatttcata tgccctgcct tggagttcac caagaagttc
1441 tcagaatggg gaaataatgc cttttctac tattttgaac accgatcctc caaacttccg
1501 tggccagaat ggatgggagt gatgcatggc tatgaaattg aatttgtctt tggtttacct
1561 ctggaagaa gagataatta cacaaaagcc gaggaaattt tgagtagatc catagtgaaa
1621 cggtgggcaa attttgcaaa atatgggaat ccaaatgaga ctcagaacaa tagcacaagc
1681 tggcctgtct tcaaaagcac tgaacaaaaa tatctaacct tgaatacaga gtcaacaaga
1741 ataatgacga aactacgtgc tcaacaatgt cgattctgga tcattttt tccaaaagtc
1801 ttggaaatga caggaaatat tgatgaagca gaatgggagt ggaaagcagg attccatcgc
1861 tggaacaatt acatgatgga ctggaaaaat caatttaacg attacactag caagaaagaa
1921 agttgtgtgg gtctctaatt aatagattta ccctttatag aacatatttt cctttagatc
1981 aaggcaaaaa tatcaggagc ttttttacac acctactaaa aaagttatta tgtagctgaa
2041 acaaaaatgc cagaaggata atattgattc ctcacatctt taacttagta ttttacctag
2101 catttcaaaa cccaaatggc tagaacatgt ttaattaaat ttcacaatat aaagttctac
2161 agttaattat gtgcatatta aaacaatggc ctggttcaat ttctttcttt ccttaataaa
2221 tttaagtttt ttccccccaa aattatcagt gctctgcttt tagtcacgtg tattttcatt
2281 accactcgta aaaaggtatc ttttttaaat gaattaaata ttgaaacact gtacaccata
2341 gtttacaata ttatgtttcc taattaaaat aagaattgaa tgtcaatatg agatattaaa
2401 ataagcacag aaaatc
```

Fig. 1

BCHE-K cDNA sequence (SEQ ID NO:2)

```
   1 tactgaatgt cagtgcagtc caatttacag gctggagcag cagctgcatc ctgcatttcc
  61 ccgaagtatt acatgatttt cactccttgc aaactttacc atctttgttg cagagaatcg
 121 gaaatcaata tgcatagcaa agtcacaatc atatgcatca gatttctctt ttggtttctt
 181 ttgctctgca tgcttattgg gaagtcacat actgaagatg acatcataat tgcaacaaag
 241 aatggaaaag tcagagggat gaacttgaca gttttggtg gcacggtaac agcctttctt
 301 ggaattccct atgcacagcc acctcttggt agacttcgat tcaaaaagcc acagtctctg
 361 accaagtggt ctgatatttg gaatgccaca aaatatgcaa attcttgctg tcagaacata
 421 gatcaaagtt tccaggctt ccatggatca gagatgtgga acccaaacac tgacctcagt
 481 gaagactgtt tatatctaaa tgtatggatt ccagcaccta accaaaaaaa tgccactgta
 541 ttgatatgga tttatggtgg tggttttcaa actggaacat catctttaca tgtttatgat
 601 ggcaagtttc tggctcgggt tgaaagagtt attgtagtgt caatgaacta tagggtgggt
 661 gccctaggat tcttagcttt gccaggaaat cctgaggctc agggaacat gggtttattt
 721 gatcaacagt tggctcttca gtgggttcaa aaaaatatag cagcctttgg tggaaatcct
 781 aaaagtgtaa ctctctttgg agaaagtgca ggagcagctt cagttagcct gcatttgctt
 841 tctcctggaa gccattcatt gttcaccaga gccattctgc aaagtggatc ctttaatgct
 901 ccttgggcgg taacatctct ttatgaagct aggaacagaa cgttgaactt agctaaattg
 961 actggttgct ctagagagaa tgagactgaa ataatcaagt gtcttagaaa taaagatccc
1021 caagaaattc ttctgaatga agcatttgtt gtcccctatg ggactccttt gtcagtaaac
1081 tttggtccga ccgtggatgg tgatttctc actgacatgc agacatatt acttgaactt
1141 ggacaattta aaaaaaccca gattttggtg ggtgttaata agatgaagg gacagctttt
1201 ttagtctatg gtgctcctgg cttcagcaaa gataacaata gtatcataac tagaaaagaa
1261 tttcaggaag gtttaaaaat attttttcca ggagtgagtg agtttggaaa ggaatccatc
1321 cttttcatt acacagactg ggtagatgat cagagacctg aaaactaccg tgaggccttg
1381 ggtgatgttg ttggggatta taatttcata tgccctgcct tggagttcac caagaagttc
1441 tcagaatggg gaaataatgc cttttctac tattgaac accgatcctc caaacttccg
1501 tggccagaat ggatgggagt gatgcatggc tatgaaattg aatttgtctt tggtttacct
1561 ctggaaagaa gagataatta cacaaaagcc gaggaaattt tgagtagatc catagtgaaa
1621 cggtgggcaa attttgcaaa atatgggaat ccaaatgaga ctcagaacaa tagcacaagc
1681 tggcctgtct tcaaaagcac tgaacaaaaa tatctaacct tgaatacaga gtcaacaaga
1741 ataatgacga aactacgtgc tcaacaatgt cgattctgga catcattttt tccaaaagtc
1801 ttggaaatga caggaaatat tgatgaaAca gaatgggagt ggaaagcagg attccatcgc
1861 tggaacaatt acatgatgga ctggaaaaat caatttaacg attacactag caagaaagaa
1921 agttgtgtgg gtctctaatt aatagattta ccctttatag aacatatttt cctttagatc
1981 aaggcaaaaa tatcaggagc tttttacac acctactaaa aaagttatta tgtagctgaa
2041 acaaaaatgc cagaaggata atattgattc ctcacatctt taacttagta ttttacctag
2101 catttcaaaa cccaaatggc tagaacatgt ttaattaaat ttcacaatat aaagttctac
2161 agttaattat gtgcatatta aaacaatggc ctggttcaat ttctttcttt ccttaataaa
2221 tttaagtttt ttccccccaa aattatcagt gctctgcttt tagtcacgtg tattttcatt
2281 accactcgta aaaggtatc tttttaaat gaattaaata ttgaaacact gtacaccata
2341 gtttacaata ttatgtttcc taattaaaat aagaattgaa tgtcaatatg agatattaaa
2401 ataagcacag aaaatc
```

Fig. 2

BCHE Amino Acid Sequence (SEQ ID NO:3)

MHSKVTIICIRFLFWFLLLCMLIGKSHTEDDIIIATKNGKVRGM
NLTVFGGTVTAFLGIPYAQPPLGRLRFKKPQSLTKWSDIWNATKYANSCCQNIDQSFP
GFHGSEMWNPNTDLSEDCLYLNVWIPAPKPKNATVLIWIYGGGFQTGTSSLHVYDGKF
LARVERVIVVSMNYRVGALGFLALPGNPEAPGNMGLFDQQLALQWVQKNIAAFGGNPK
SVTLFGESAGAASVSLHLLSPGSHSLFTRAILQSGSFNAPWAVTSLYEARNRTLNLAK
LTGCSRENETEIIKCLRNKDPQEILLNEAFVVPYGTPLSVNFGPTVDGDFLTDMPDIL
LELGQFKKTQILVGVNKDEGTAFLVYGAPGFSKDNNSIITRKEFQEGLKIFFPGVSEF
GKESILFHYTDWVDDQRPENYREALGDVVGDYNFICPALEFTKKFSEWGNNAFFYYFE
HRSSKLPWPEWMGVMHGYEIEFVFGLPLERRDNYTKAEEILSRSIVKRWANFAKYGNP
NETQNNSTSWPVFKSTEQKYLTLNTESTRIMTKLRAQQCRFWTSFFPKVLEMTGNIDE
AEWEWKAGFHRWNNYMMDWKNQFNDYTSKKESCVGL

Fig. 3

BCHE-K Amino Acid Sequence (SEQ ID NO:4)

```
            MHSKVTIICIRFLFWFLLLCMLIGKSHTEDDIIIATKNGKVRGM
NLTVFGGTVTAFLGIPYAQPPLGRLRFKKPQSLTKWSDIWNATKYANSCCQNIDQSFP
GFHGSEMWNPNTDLSEDCLYLNVWIPAPKPKNATVLIWIYGGGFQTGTSSLHVYDGKF
LARVERVIVVSMNYRVGALGFLALPGNPEAPGNMGLFDQQLALQWVQKNIAAFGGNPK
SVTLFGESAGAASVSLHLLSPGSHSLFTRAILQSGSFNAPWAVTSLYEARNRTLNLAK
LTGCSRENETEIIKCLRNKDPQEILLNEAFVVPYGTPLSVNFGPTVDGDFLTDMPDIL
LELGQFKKTQILVGVNKDEGTAFLVYGAPGFSKDNNSIITRKEFQEGLKIFFPGVSEF
GKESILFHYTDWVDDQRPENYREALGDVVGDYNFICPALEFTKKFSEWGNNAFFYYFE
HRSSKLPWPEWMGVMHGYEIEFVFGLPLERRDNYTKAEEILSRSIVKRWANFAKYGNP
NETQNNSTWPVFKSTEQKYLTLNTESTRIMTKLRAQQCRFWTSFFPKVLEMTGNIDE
TEWEWKAGFHRWNNYMMDWKNQFNDYTSKKESCVGL
```

Fig. 4

SEQUENCE LISTING

<160> NUMBER OF SEQ ID NOS: 8

<210> SEQ ID NO 1
<211> LENGTH: 2416
<212> TYPE: DNA
<213> ORGANISM: Homo sapiens

<400> SEQUENCE: 1
tactgaatgt cagtgcagtc caatttacag gctggagcag cagctgcatc ctgcatttcc    60

-continued

```
ccgaagtatt acatgatttt cactccttgc aaactttacc atctttgttg cagagaatcg      120
gaaatcaata tgcatagcaa agtcacaatc atatgcatca gatttctctt ttggtttctt      180
ttgctctgca tgcttattgg gaagtcacat actgaagatg acatcataat tgcaacaaag      240
aatggaaaag tcagagggat gaacttgaca gttttttggtg gcacggtaac agcctttctt    300
ggaattccct atgcacagcc acctcttggt agacttcgat tcaaaaagcc acagtctctg      360
accaagtggt ctgatatttg gaatgccaca aaatatgcaa attcttgctg tcagaacata     420
gatcaaagtt ttccaggctt ccatggatca gagatgtgga acccaaacac tgacctcagt     480
gaagactgtt tatatctaaa tgtatggatt ccagcaccta aaccaaaaaa tgccactgta     540
ttgatatgga tttatggtgg tggttttcaa actggaacat catctttaca tgtttatgat    600
ggcaagtttc tggctcgggt tgaaagagtt attgtagtgt caatgaacta tagggtgggt    660
gccctaggat tcttagcttt gccaggaaat cctgaggctc agggaacat gggtttattt      720 gatcaacagt tggctcttca gtgggttcaa aaaaatatag cagcctttgg tggaaatcct    780
aaaagtgtaa ctctctttgg agaaagtgca ggagcagctt cagttagcct gcatttgctt    840
tctcctggaa gccattcatt gttcaccaga gccattctgc aaagtggatc ctttaatgct   900
ccttgggcgg taacatctct ttatgaagct aggaacagaa cgttgaactt agctaaattg    960
actggttgct ctagagagaa tgagactgaa ataatcaagt gtcttagaaa taaagatccc    1020
caagaaattc ttctgaatga agcatttgtt gtccctatg ggactccttt gtcagtaaac   1080
tttggtccga ccgtggatgg tgattttctc actgacatgc cagacatatt acttgaactt    1140
ggacaattta aaaaaaccca gattttggtg ggtgttaata agatgaagg acagcttttt    1200 ttagtctatg gtgctcctgg cttcagcaaa gataacaata gtatcataac tagaaaagaa    1260
tttcaggaag gtttaaaaat attttttcca ggagtgagtg agtttggaaa ggaatccatc    1320 cttttcatt acacagactg ggtagatgat cagagacctg aaaactaccg tgaggccttg    1380
ggtgatgttg ttggggatta taatttcata tgccctgcct tggagttcac caagaagttc    1440
tcagaatggg gaaataatgc cttttctac tattttgaac accgatcctc caaacttccg    1500
tggccagaat ggatgggagt gatgcatggc tatgaaattg aatttgtctt tggtttacct    1560
ctggaaagaa gagataatta cacaaaagcc gaggaaattt tgagtagatc catagtgaaa    1620
cggtgggcaa attttgcaaa atatgggaat ccaaatgaga ctcagaacaa tagcacaagc    1680
tggcctgtct tcaaaagcac tgaacaaaaa tatctaacct tgaatacaga gtcaacaaga    1740
ataatgacga aactacgtgc tcaacaatgt cgattctgga catcattttt tccaaaagtc    1800
ttggaaatga caggaaatat tgatgaagca gaatgggagt ggaaagcagg attccatcgc    1860
tggaacaatt acatgatgga ctggaaaaat caatttaacg attacactag caagaaagaa    1920
agttgtgtgg gtctctaatt aatagattta ccctttatag aacatatttt cctttagatc    1980
aaggcaaaaa tatcaggagc ttttttacac acctactaaa aaagttatta tgtagctgaa    2040
acaaaaatgc cagaaggata atattgattc ctcacatctt taacttagta ttttacctag    2100
catttcaaaa cccaaatggc tagaacatgt ttaattaaat ttcacaatat aaagttctac    2160
agttaattat gtgcatatta aaacaatggc ctggttcaat ttctttctttt ccttaataaa    2220 tttaagtttt ttccccccaa aattatcagt gctctgcttt tagtcacgtg tattttcatt    2280
accactcgta aaaggtatc ttttttaaat gaattaaata ttgaaacact gtacaccata    2340
gtttacaata ttatgttttcc taattaaaat aagaattgaa tgtcaatatg agatattaaa    2400
ataagcacag aaaatc                                                     2416
```

<210> SEQ ID NO 2
<211> LENGTH: 2416
<212> TYPE: DNA
<213> ORGANISM: Homo sapiens

<400> SEQUENCE: 2

| | | | | | |
|---|---|---|---|---|---|
| tactgaatgt | cagtgcagtc | caatttacag | gctggagcag | cagctgcatc | ctgcatttcc | 60 |
| ccgaagtatt | acatgatttt | cactccttgc | aaactttacc | atctttgttg | cagagaatcg | 120 |
| gaaatcaata | tgcatagcaa | agtcacaatc | atatgcatca | gatttctctt | ttggtttctt | 180 |
| ttgctctgca | tgcttattgg | gaagtcacat | actgaagatg | acatcataat | tgcaacaaag | 240 |
| aatggaaaag | tcagagggat | gaacttgaca | gttttggtg | gcacggtaac | agcctttctt | 300 |
| ggaattccct | atgcacagcc | acctcttggt | agacttcgat | tcaaaaagcc | acagtctctg | 360 |
| accaagtggt | ctgatatttg | gaatgccaca | aaatatgcaa | attcttgctg | tcagaacata | 420 |
| gatcaaagtt | ttccaggctt | ccatggatca | gagatgtgga | acccaaacac | tgacctcagt | 480 |
| gaagactgtt | tatatctaaa | tgtatggatt | ccagcaccta | accaaaaaa | tgccactgta | 540 |
| ttgatatgga | tttatggtgg | tggttttcaa | actggaacat | catctttaca | tgtttatgat | 600 |
| ggcaagtttc | tggctcgggt | tgaaagagtt | attgtagtgt | caatgaacta | tagggtgggt | 660 |
| gccctaggat | tcttagcttt | gccaggaaat | cctgaggctc | cagggaacat | gggtttattt | 720 |
| gatcaacagt | tggctcttca | gtgggttcaa | aaaatatag | cagccttggg | tggaaatcct | 780 |
| aaaagtgtaa | ctctctttgg | agaaagtgca | ggagcagctt | cagttagcct | gcatttgctt | 840 |
| tctcctggaa | gccattcatt | gttcaccaga | gccattctgc | aaagtggatc | ctttaatgct | 900 |
| ccttgggcgg | taacatctct | ttatgaagct | aggaacagaa | cgttgaactt | agctaaattg | 960 |
| actggttgct | ctagagagaa | tgagactgaa | ataatcaagt | gtcttagaaa | taaagatccc | 1020 |
| caagaaattc | ttctgaatga | agcatttgtt | gtcccctatg | ggactccttt | gtcagtaaac | 1080 |
| tttggtccga | ccgtggatgg | tgattttctc | actgacatgc | cagacatatt | acttgaactt | 1140 |
| ggacaattta | aaaaaaccca | gattttggtg | ggtgttaata | aagatgaagg | gacagctttt | 1200 |
| ttagtctatg | gtgctcctgg | cttcagcaaa | gataacaata | gtatcataac | tagaaaagaa | 1260 |
| tttcaggaag | gtttaaaaat | attttttcca | ggagtgagtg | agtttggaaa | ggaatccatc | 1320 |
| cttttttcatt | acacagactg | ggtagatgat | cagagacctg | aaaactaccg | tgaggccttg | 1380 |
| ggtgatgttg | ttgggggatta | taatttcata | tgccctgcct | tggagttcac | caagaagttc | 1440 |
| tcagaatggg | gaaataatgc | ctttttctac | tattttgaac | accgatcctc | caaacttccg | 1500 |
| tggccagaat | ggatgggagt | gatgcatggc | tatgaaattg | aatttgtctt | tggtttacct | 1560 |
| ctggaaagaa | gagataatta | cacaaaagcc | gaggaaattt | tgagtagatc | catagtgaaa | 1620 |
| cggtgggcaa | attttgcaaa | atatgggaat | ccaaatgaga | ctcagaacaa | tagcacaagc | 1680 |
| tggcctgtct | tcaaaagcac | tgaacaaaaa | tatctaacct | tgaatacaga | gtcaacaaga | 1740 |
| ataatgacga | aactacgtgc | tcaacaatgt | cgattctgga | catcattttt | tccaaaagtc | 1800 |
| ttggaaatga | caggaaatat | tgatgaaaca | gaatgggagt | ggaaagcagg | attccatcgc | 1860 |
| tggaacaatt | acatgatgga | ctggaaaaat | caatttaacg | attacactag | caagaaagaa | 1920 |
| agttgtgtgg | gtctctaatt | aatagattta | ccctttatag | aacatatttt | cctttagatc | 1980 |
| aaggcaaaaa | tatcaggagc | ttttttacac | acctactaaa | aaagttatta | tgtagctgaa | 2040 |
| acaaaaatgc | cagaaggata | atattgattc | ctcacatctt | taacttagta | ttttacctag | 2100 |

-continued

```
catttcaaaa cccaaatggc tagaacatgt ttaattaaat ttcacaatat aaagttctac    2160
agttaattat gtgcatatta aaacaatggc ctggttcaat ttctttcttt ccttaataaa    2220
tttaagtttt ttcccccaa aattatcagt gctctgcttt tagtcacgtg tattttcatt    2280
accactcgta aaaggtatc ttttttaaat gaattaaata ttgaaacact gtacaccata    2340
gtttacaata ttatgtttcc taattaaaat aagaattgaa tgtcaatatg agatattaaa    2400
ataagcacag aaaatc                                                    2416
```

<210> SEQ ID NO 3
<211> LENGTH: 602
<212> TYPE: PRT
<213> ORGANISM: Homo sapiens

<400> SEQUENCE: 3

```
Met His Ser Lys Val Thr Ile Ile Cys Ile Arg Phe Leu Phe Trp Phe
 1               5                   10                  15

Leu Leu Leu Cys Met Leu Ile Gly Lys Ser His Thr Glu Asp Asp Ile
             20                  25                  30

Ile Ile Ala Thr Lys Asn Gly Lys Val Arg Gly Met Asn Leu Thr Val
         35                  40                  45

Phe Gly Gly Thr Val Thr Ala Phe Leu Gly Ile Pro Tyr Ala Gln Pro
     50                  55                  60

Pro Leu Gly Arg Leu Arg Phe Lys Lys Pro Gln Ser Leu Thr Lys Trp
 65                  70                  75                  80

Ser Asp Ile Trp Asn Ala Thr Lys Tyr Ala Asn Ser Cys Cys Gln Asn
                 85                  90                  95

Ile Asp Gln Ser Phe Pro Gly Phe His Gly Ser Glu Met Trp Asn Pro
            100                 105                 110

Asn Thr Asp Leu Ser Glu Asp Cys Leu Tyr Leu Asn Val Trp Ile Pro
        115                 120                 125

Ala Pro Lys Pro Lys Asn Ala Thr Val Leu Ile Trp Ile Tyr Gly Gly
    130                 135                 140

Gly Phe Gln Thr Gly Thr Ser Ser Leu His Val Tyr Asp Gly Lys Phe
145                 150                 155                 160

Leu Ala Arg Val Glu Arg Val Ile Val Val Ser Met Asn Tyr Arg Val
                165                 170                 175

Gly Ala Leu Gly Phe Leu Ala Leu Pro Gly Asn Pro Glu Ala Pro Gly
            180                 185                 190

Asn Met Gly Leu Phe Asp Gln Gln Leu Ala Leu Gln Trp Val Gln Lys
        195                 200                 205

Asn Ile Ala Ala Phe Gly Gly Asn Pro Lys Ser Val Thr Leu Phe Gly
    210                 215                 220

Glu Ser Ala Gly Ala Ala Ser Val Ser Leu His Leu Leu Ser Pro Gly
225                 230                 235                 240

Ser His Ser Leu Phe Thr Arg Ala Ile Leu Gln Ser Gly Ser Phe Asn
                245                 250                 255

Ala Pro Trp Ala Val Thr Ser Leu Tyr Glu Ala Arg Asn Arg Thr Leu
            260                 265                 270

Asn Leu Ala Lys Leu Thr Gly Cys Ser Arg Glu Asn Glu Thr Glu Ile
        275                 280                 285

Ile Lys Cys Leu Arg Asn Lys Asp Pro Gln Glu Ile Leu Leu Asn Glu
    290                 295                 300

Ala Phe Val Val Pro Tyr Gly Thr Pro Leu Ser Val Asn Phe Gly Pro
305                 310                 315                 320
```

```
Thr Val Asp Gly Asp Phe Leu Thr Asp Met Pro Asp Ile Leu Leu Glu
                325                 330                 335

Leu Gly Gln Phe Lys Lys Thr Gln Ile Leu Val Gly Val Asn Lys Asp
            340                 345                 350

Glu Gly Thr Ala Phe Leu Val Tyr Gly Ala Pro Gly Phe Ser Lys Asp
        355                 360                 365

Asn Asn Ser Ile Ile Thr Arg Lys Glu Phe Gln Glu Gly Leu Lys Ile
    370                 375                 380

Phe Phe Pro Gly Val Ser Glu Phe Gly Lys Glu Ser Ile Leu Phe His
385                 390                 395                 400

Tyr Thr Asp Trp Val Asp Asp Gln Arg Pro Glu Asn Tyr Arg Glu Ala
                405                 410                 415

Leu Gly Asp Val Val Gly Asp Tyr Asn Phe Ile Cys Pro Ala Leu Glu
            420                 425                 430

Phe Thr Lys Lys Phe Ser Glu Trp Gly Asn Asn Ala Phe Phe Tyr Tyr
        435                 440                 445

Phe Glu His Arg Ser Ser Lys Leu Pro Trp Pro Glu Trp Met Gly Val
    450                 455                 460

Met His Gly Tyr Glu Ile Glu Phe Val Phe Gly Leu Pro Leu Glu Arg
465                 470                 475                 480

Arg Asp Asn Tyr Thr Lys Ala Glu Glu Ile Leu Ser Arg Ser Ile Val
                485                 490                 495

Lys Arg Trp Ala Asn Phe Ala Lys Tyr Gly Asn Pro Asn Glu Thr Gln
            500                 505                 510

Asn Asn Ser Thr Ser Trp Pro Val Phe Lys Ser Thr Glu Gln Lys Tyr
        515                 520                 525

Leu Thr Leu Asn Thr Glu Ser Thr Arg Ile Met Thr Lys Leu Arg Ala
    530                 535                 540

Gln Gln Cys Arg Phe Trp Thr Ser Phe Phe Pro Lys Val Leu Glu Met
545                 550                 555                 560

Thr Gly Asn Ile Asp Glu Ala Glu Trp Glu Trp Lys Ala Gly Phe His
                565                 570                 575

Arg Trp Asn Asn Tyr Met Met Asp Trp Lys Asn Gln Phe Asn Asp Tyr
            580                 585                 590

Thr Ser Lys Lys Glu Ser Cys Val Gly Leu
        595                 600

<210> SEQ ID NO 4
<211> LENGTH: 602
<212> TYPE: PRT
<213> ORGANISM: Homo sapiens

<400> SEQUENCE: 4

Met His Ser Lys Val Thr Ile Ile Cys Ile Arg Phe Leu Phe Trp Phe
 1               5                  10                  15

Leu Leu Leu Cys Met Leu Ile Gly Lys Ser His Thr Glu Asp Asp Ile
            20                  25                  30

Ile Ile Ala Thr Lys Asn Gly Lys Val Arg Gly Met Asn Leu Thr Val
        35                  40                  45

Phe Gly Gly Thr Val Thr Ala Phe Leu Gly Ile Pro Tyr Ala Gln Pro
    50                  55                  60

Pro Leu Gly Arg Leu Arg Phe Lys Lys Pro Gln Ser Leu Thr Lys Trp
65                  70                  75                  80

Ser Asp Ile Trp Asn Ala Thr Lys Tyr Ala Asn Ser Cys Cys Gln Asn
```

-continued

```
                85                  90                  95
Ile Asp Gln Ser Phe Pro Gly Phe His Gly Ser Glu Met Trp Asn Pro
                    100                 105                 110

Asn Thr Asp Leu Ser Glu Asp Cys Leu Tyr Leu Asn Val Trp Ile Pro
            115                 120                 125

Ala Pro Lys Pro Lys Asn Ala Thr Val Leu Ile Trp Ile Tyr Gly Gly
130                 135                 140

Gly Phe Gln Thr Gly Thr Ser Ser Leu His Val Tyr Asp Gly Lys Phe
145                 150                 155                 160

Leu Ala Arg Val Glu Arg Val Ile Val Ser Met Asn Tyr Arg Val
                165                 170                 175

Gly Ala Leu Gly Phe Leu Ala Leu Pro Gly Asn Pro Glu Ala Pro Gly
                180                 185                 190

Asn Met Gly Leu Phe Asp Gln Gln Leu Ala Leu Gln Trp Val Gln Lys
            195                 200                 205

Asn Ile Ala Ala Phe Gly Gly Asn Pro Lys Ser Val Thr Leu Phe Gly
            210                 215                 220

Glu Ser Ala Gly Ala Ala Ser Val Ser Leu His Leu Leu Ser Pro Gly
225                 230                 235                 240

Ser His Ser Leu Phe Thr Arg Ala Ile Leu Gln Ser Gly Ser Phe Asn
                245                 250                 255

Ala Pro Trp Ala Val Thr Ser Leu Tyr Glu Ala Arg Asn Arg Thr Leu
            260                 265                 270

Asn Leu Ala Lys Leu Thr Gly Cys Ser Arg Glu Asn Glu Thr Glu Ile
            275                 280                 285

Ile Lys Cys Leu Arg Asn Lys Asp Pro Gln Glu Ile Leu Leu Asn Glu
            290                 295                 300

Ala Phe Val Val Pro Tyr Gly Thr Pro Leu Ser Val Asn Phe Gly Pro
305                 310                 315                 320

Thr Val Asp Gly Asp Phe Leu Thr Asp Met Pro Asp Ile Leu Leu Glu
                325                 330                 335

Leu Gly Gln Phe Lys Lys Thr Gln Ile Leu Val Gly Val Asn Lys Asp
            340                 345                 350

Glu Gly Thr Ala Phe Leu Val Tyr Gly Ala Pro Gly Phe Ser Lys Asp
            355                 360                 365

Asn Asn Ser Ile Ile Thr Arg Lys Glu Phe Gln Glu Gly Leu Lys Ile
            370                 375                 380

Phe Phe Pro Gly Val Ser Glu Phe Gly Lys Glu Ser Ile Leu Phe His
385                 390                 395                 400

Tyr Thr Asp Trp Val Asp Asp Gln Arg Pro Glu Asn Tyr Arg Glu Ala
                405                 410                 415

Leu Gly Asp Val Val Gly Asp Tyr Asn Phe Ile Cys Pro Ala Leu Glu
                420                 425                 430

Phe Thr Lys Lys Phe Ser Glu Trp Gly Asn Asn Ala Phe Phe Tyr Tyr
            435                 440                 445

Phe Glu His Arg Ser Ser Lys Leu Pro Trp Pro Glu Trp Met Gly Val
            450                 455                 460

Met His Gly Tyr Glu Ile Glu Phe Val Phe Gly Leu Pro Leu Glu Arg
465                 470                 475                 480

Arg Asp Asn Tyr Thr Lys Ala Glu Glu Ile Leu Ser Arg Ser Ile Val
                485                 490                 495

Lys Arg Trp Ala Asn Phe Ala Lys Tyr Gly Asn Pro Asn Glu Thr Gln
            500                 505                 510
```

```
Asn Asn Ser Thr Ser Trp Pro Val Phe Lys Ser Thr Glu Gln Lys Tyr
        515                 520                 525
Leu Thr Leu Asn Thr Glu Ser Thr Arg Ile Met Thr Lys Leu Arg Ala
        530                 535                 540
Gln Gln Cys Arg Phe Trp Thr Ser Phe Phe Pro Lys Val Leu Glu Met
545                 550                 555                 560
Thr Gly Asn Ile Asp Glu Thr Glu Trp Glu Trp Lys Ala Gly Phe His
                565                 570                 575
Arg Trp Asn Asn Tyr Met Met Asp Trp Lys Asn Gln Phe Asn Asp Tyr
            580                 585                 590
Thr Ser Lys Lys Glu Ser Cys Val Gly Leu
        595                 600

<210> SEQ ID NO 5
<211> LENGTH: 27
<212> TYPE: DNA
<213> ORGANISM: Homo sapiens

<400> SEQUENCE: 5
ctgtactgtg tagttagaga aaatggc                                    27

<210> SEQ ID NO 6
<211> LENGTH: 30
<212> TYPE: DNA
<213> ORGANISM: Homo sapiens

<400> SEQUENCE: 6
tttttacgag tggtaatgaa aatacacgtg                                 30

<210> SEQ ID NO 7
<211> LENGTH: 26
<212> TYPE: DNA
<213> ORGANISM: Homo sapiens

<400> SEQUENCE: 7
ccacacaact ttctttcttg ctagtg                                     26

<210> SEQ ID NO 8
<211> LENGTH: 26
<212> TYPE: DNA
<213> ORGANISM: Homo sapiens

<400> SEQUENCE: 8
gccttttgta ttcgaaatta tttttc                                     26
```

METHODS FOR TREATING A NEUROLOGICAL DISEASE BY DETERMINING BCHE GENOTYPE

This Application claims benefit of Provisional application Ser. No 60/089,406 filed Jun. 16, 1998.

BACKGROUND OF THE INVENTION

In general, the invention relates to methods for treating a neurological disease. Neurological diseases, for example, Alzheimer's disease, provide a unique series of complications for clinicians, patients, and care givers; the diseases often progress rapidly and disrupt a vast number of major life functions. The progressive nature of these diseases makes the passage of time a crucial issue in the treatment process. Treatment choices for neurological diseases, particularly those affecting cognitive function, can be complicated by the fact that it often takes a significant period of treatment to determine if a given therapy is effective. Accordingly, treatment with the most effective drug or drugs is often delayed while the disease continues to progress. A method that would allow one to predict which patients will respond to a specific therapy would provide physical and psychological benefits. As healthcare becomes increasingly inaccessible, the ability to allocate healthcare resources effectively also becomes more important.

SUMMARY OF THE INVENTION

The present invention provides a method for treating a patient at risk for a neurological disease, or diagnosed with a neurological disease. The methods include identifying such a patient and determining the patient's BCHE allele status. The invention provides a method for using the patient's BCHE allele status to determine a treatment protocol which includes a prediction of the efficacy of a therapy for the treatment of a neurological disease. In a related aspect, the invention features a treatment protocol that provides a prediction of patient outcome.

In another related aspect, the invention provides a method for identifying a patient for participation in a clinical trial of a therapy for the treatment of a neurological disease. The method involves characterizing a patient with a disease risk and determining the patient's BCHE allele status. In yet another related aspect, the method further involves determining the patient's BCHE allele status and selecting those patients having at least one wild type BCHE allele, preferably having two wild type BCHE alleles, as candidates likely to respond to a therapy for the treatment of a neurological disease. In a preferred embodiment, the treatment protocol involves a comparison of the BCHE allele status of a patient with a control population and a responder population. This comparison allows for a statistical calculation of a patient's likelihood of responding to a therapy.

In preferred embodiments of two of the above aspects, the prediction of drug efficacy involves cholinomimetic therapies, preferably tacrine, or non-cholinomimetic therapies, preferably a vasopressinergic drug that will be effective in patients with the genotype of at least one non-BCHE-K allele, and preferably two non-BCHE-K alleles. In a preferred embodiment, the invention provides a treatment protocol that utilizes one of the following therapies for a neurological disease: probucol, a monoamine oxidase inhibitor, muscarinic agonist, neurotrophic factor, noradrenergic factor, antioxidant, anti-inflammatory, corticotrophin-releasing hormone (CRH), somatostatin, substance P, neuropeptide Y, or thyrotrophin-releasing hormone (TRH).

In a particular application of the invention, all of the above aspects feature a determination of the BCHE allele status of the patient, where a determination of the patient's BCHE-K allele status as being heterozygous or homozygous, is predictive of the patient having a poor response to a therapy for a neurological disease. In a preferred embodiment, the above methods are used for treating a neurological disease such as Alzheimer's disease, neurofibromatosis, Huntington's disease, depression, amyotrophic lateral sclerosis, multiple sclerosis, stroke, Parkinson's disease, or multi-infarct dementia. In another preferred embodiment, the invention is suitable for treating a patient with a non-AD neurological disease.

In another aspect, the invention provides a method for treating a patient at risk for a non-AD neurological disease by a) identifying a patient with a risk, b) determining the BCHE allele status of the patient, and c) converting the data obtained in step b) into a treatment protocol that includes a comparison of the BCHE allele status with the allele frequency of a control population. This comparison allows for a statistical calculation of the patient's risk for having a non-AD neurological disease. In preferred embodiments, the method provides a treatment protocol that predicts a patient being heterozygous or homozygous for the BCHE-K allele to respond poorly to a cholinomimetic (e.g., tacrine) or specific non-cholinomimetic (e.g., vasopressinergics) therapy for a neurological disease, and a patient who is wild type BCHE homozygous, to respond favorably to the therapy.

In a related aspect, the invention provides treating a patient at risk for or diagnosed with a neurological disease using the above method, and conducting an additional step c) which involves determining the apoE allele load status of the patient. This method further involves converting the data obtained in steps b) and c) into a treatment protocol that includes a comparison of the allele status of these steps with the allele frequency of a control population. This affords a statistical calculation of the patient's risk for having a neurological disease. In a preferred embodiment, the method is useful for treating a neurological disease such as Alzheimer's disease, neurofibromatosis, Huntington's disease, depression, amyotrophic lateral sclerosis, multiple sclerosis, stroke, Parkinson's disease, or multi-infarct dementia. In addition, in related embodiments, the methods provide a treatment protocol that predicts a patient to be at high risk for a neurological disease and responding poorly to a cholinomimetic or particular non-cholinomimetic therapy (e.g., vasopressinergics) if the patient is determined to have both an apoE4 allele and a BCHE-K allele. Such patients are preferably given an alternative therapy.

The invention also provides a method for improving the efficacy of a therapy for the treatment of neurological diseases. The method includes the step of comparing the relative efficacy of the therapy in patients having different BCHE alleles. Preferably, administration of the drug is preferentially provided to those patients with a BCHE allele type associated with increased efficacy. In a preferred embodiment, the alleles of BCHE used are wild type BCHE and BCHE associated with reduced biological activity. Most preferably the allele associated with reduced biological activity is BCHE-K.

As used herein, by "therapy for the treatment of a neurological disease" is meant any therapy suitable for treating a neurological disease. A suitable therapy can be a pharmacological agent or drug that may enhance cognitive function, motor function, or neuronal activity of the central nervous system, peripheral nervous system, or inhibit the further deterioration of any of these faculties.

By "cholinomimetic therapy" is meant any drug that mimics the function of acetylcholine or enhances the activity of acetylcholine synthesizing cells. These drugs include, but are not limited to, inhibitors of acetylcholine degradation (acetylcholine esterase inhibitors such as tacrine), drugs that mimic acetylcholine structure and function, drugs that block acetylcholine uptake by neurons, and drugs that interact with pre-synaptic receptors to induce acetylcholine release from cholinergic neurons.

By "non-cholinomimetic vasopressinergic therapy" is meant a therapy that utilizes a vasopressinergic modulator such as, for example, S12024 (provided by Servier, Les Laboratoires Servier, 22 rue Garnier, 92200 Neuilly sur Seine, France).

By "non-AD neurological disease" is meant a disease other than Alzheimer's disease, which involves the neuronal cells of the nervous system. Specifically included are: prion diseases (e.g., Creutzfeldt-Jakob disease); pathologies of the developing brain (e.g., congenital defects in amino acid metabolism, such as argininosuccinicaciduria, cystathioninuria, histidinemia, homocystinuria, hyperammonemia, phenylketonuria, tyrosinemia, and fragile X syndrome); pathologies of the mature brain (e.g., neurofibromatosis, Huntington's disease, depression, amyotrophic lateral sclerosis, multiple sclerosis); conditions that strike in adulthood (e.g. Creutzfeldt-Jakob disease, Lewy body disease, Parkinson's disease, Pick's disease); and other pathologies of the brain (e.g., brain mishaps, brain injury, coma, infections by various agents, dietary deficiencies, stroke, multi-infarct dementia, and cardiovascular accidents).

By "Alzheimer's Disease (AD)" is meant a pathology characterized by an early and extensive loss of entorhinal cortex neurons. AD patients may be identified by progressive and degenerative effects on the brain which are not attributable to other causes. Post-mortem, the disease may be diagnosed by the presence of amyloid plaques and fibrils.

By "drug efficacy" is meant the determination of an appropriate drug, drug dosage, administration schedule, and prediction of therapeutic utility.

By "apoE4 allele load" is meant the relative ratio of apoE2, 3, and 4 alleles in the patient's chromosomal DNA. The allele load may be determined by comparing the relative numbers of the patient's already known apoE allele types.

By "apoE4 allele" is meant a particular apoE isoform that can be distinguished from other apoE isoforms (e.g., apoE2 or apoE3) using the methods of the invention.

By "PCR, RT-PCR, or ligase chain reaction amplification" is meant subjecting a DNA sample to a Polymerase Chain Reaction step or ligase-mediated chain reaction step, or RNA to a RT-PCR step, such that, in the presence of appropriately designed primers, a nucleic acid fragment is synthesized or fails to be synthesized, thereby revealing the allele status of a patient. The nucleic acid may be further analyzed by DNA sequencing using techniques known in the art.

By "BCHE allele status" is meant a determination of the relative ratio of wild type butyrylcholinesterase alleles compared to an allelic variant that may encode a butyrylcholinesterase gene product of reduced catalytic activity. This may be accomplished by nucleic acid sequencing, RT-PCR, PCR, examination of the BChE protein, a determination of the BChE enzyme activity, or by other methods available to those skilled in the art.

By "BCHE-K allele (k-allele)" is meant a polymorphism of the butyrylcholinesterase (BCHE) gene which involves a point mutation at nucleotide 1828 that changes amino acid residue 539 from alanine to threonine and can result in an enzyme with reduced catalytic activity.

By "treatment protocol" is meant a therapy plan for a patient using genetic and diagnostic data, including the patient's neurological diagnosis and BCHE and ApoE genotypes. The protocol enhances therapeutic options and clarifies prognoses. The treatment protocol may include an indication of whether or not the patient is likely to respond positively to a cholinomimetic or non-cholinomimetic therapy. The treatment protocol may also include an indication of appropriate drug dose, recovery time, age of disease onset, rehabilitation time, symptomology of attacks, and risk for future disease. A treatment protocol, including any of the above aspects, may also be formulated for asymptomatic and healthy subjects in order to forecast future disease risks and determine what preventive therapies should be considered or invoked in order to decrease these disease risks. The treatment protocol may include the use of a computer software program to analyze patient data.

By "patient at risk for a neurological disease" is meant a patient identified or diagnosed as having a neurological disease, or having a genetic predisposition or risk for acquiring a neurological disease using the methods of the invention and techniques available to those skilled in the art.

By "converting" is meant compiling genotype determinations to predict either prognosis, drug efficacy, or suitability of a patient for participating in clinical trials of a neurological disease therapeutic. For example, the genotype may be compiled with other patient parameters such as age, sex, disease diagnosis, and known allelic frequency of a representative control population. The converting step may provide a determination of the statistical probability of the patient having a particular disease risk, drug response, or patient outcome.

By "prediction of patient outcome" is meant a forecast of the patient's likely health status. This may include a prediction of the patient's response to therapy, rehabilitation time, recovery time, cure rate, rate of disease progression, predisposition for future disease, or risk of having relapse.

By "therapy for the treatment of a neurological disease" is meant any pharmacological agent or drug with the property of healing, curing, or ameliorating any symptom or disease mechanism associated with a neurological disease.

By "responder population" is meant a patient or patients who respond favorably to a given therapy.

The present invention provides a number of advantages. For example, the methods described herein allow for use of a determination of a patient's BCHE genotype for the timely administration of the most suitable therapy for that particular patient.

Other features and advantages of the invention will be apparent from the following detailed description and from the claims.

DETAILED DESCRIPTION OF THE INVENTION

The drawings will first be described.

BRIEF DESCRIPTION OF THE DRAWINGS

FIG. 1 is a depiction of the cDNA sequence of the wild type human butyrylcholinesterase gene (BCHE; SEQ ID NO: 1).

FIG. 2 is a depiction of the cDNA sequence of the human butyrylcholinesterase K-allele (BCHE-K) with the single nucleotide polymorphism at base 1828 indicated in bold (SEQ ID NO: 2).

FIG. 3 is a depiction of the amino acid sequence of the wild type human butyrylcholinesterase protein (BCHE; SEQ ID NO: 3).

FIG. 4 is a depiction of the amino acid sequence of the human butyrylcholinesterase-K protein (BCHE-K) with the single amino acid residue change, from an alanine (A) to a threonine (T), indicated in bold (SEQ ID NO: 4).

Figure 5:
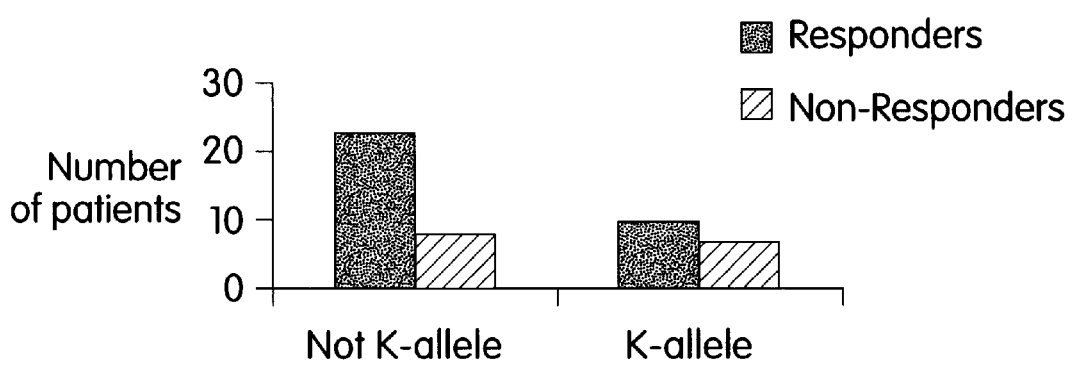
FIG. 5 is a graphical depiction of the impact the BCHE-K allele has on the efficacy of tacrine treatment in patents diagnosed with AD.

The invention described herein features methods for determining the appropriate therapy for a patient at risk for a neurological disease based on an analysis of the patient's BCHE allele status. Specifically, the presence of at least one BCHE-K allele indicates that a patient will respond poorly to cholinomimetic and non-cholinomimetic therapies such as vasopressinergics. In a preferred approach, the patient's BCHE-K allele status is rapidly diagnosed using a sensitive PCR assay and a treatment protocol is rendered. The invention also provides a method for forecasting patient outcome and the suitability of the patient for entering a clinical drug trial for the testing of a therapy for a neurological disease.

The findings described herein indicate the predictive value of the BCHE-K allele in treating patients at risk for a neurological disease such as Alzheimer's disease (AD). In addition, because the underlying mechanism influenced by the BCHE allele status is not disease-specific, the BCHE-allele status is suitable for making patient predictions for non-AD neurological diseases as well.

The following examples, which describe preferred techniques and experimental results, are provided for the purpose of illustrating the invention, and should not be construed as limiting.

EXAMPLE 1

Methods for Determining BCHE-K or ApoE4 Allele Status

As described above, the present invention provides a technique for efficiently treating a patient with a neurological disease risk based on their BCHE genotype.

The butyrylcholinesterase (BCHE) gene product is expressed in most human tissues, but its precise metabolic function in the body is still unknown. We have found that the polymorphic gene variant BCHE-K, consisting of a point mutation at nucleotide 1828 (GCA to ACA) which changes alanine 539 to threonine and can result in reduced catalytic activity (see FIGS. 1–4), has strong predictive value for determining if cholinomimetic (e.g., tacrine) or non-cholinomimetic (e.g., vasopressinergics) therapies will help a patient at risk for a neurological disease.

To demonstrate the effectiveness of the BCHE-K allele as a prognostic indicator in patients with a neurological disease risk, we determined the BCHE-K allele load in a large number of patients diagnosed with Alzheimer's disease. In addition, to determine if the BCHE-K polymorphism correlated with other markers associated with a neurological disease, we also genotyped these patients for the presence of the apoE4 allele and determined the predictive value of this marker when used separately or together with the BCHE-K allele status determination.

To obtain DNA for genotyping we isolated genomic DNA from whole blood according to the Gustincich method (Gustincich S., et al. *Biotechniques* 11, 298–300 (1991). This method allowed for the rapid extraction of high quality genomic DNA from whole human blood, or alternatively, directly from a patient's serum.

Genotyping was then performed by subjecting nucleic acid samples encoding the BCHE gene to a polymerase chain reaction (PCR) amplification step followed by another round of PCR amplification using a nested PCR protocol. These amplification reactions were conducted using a PCR-Express™ thermal cycler from Hybaid. The first round of PCR amplification was conducted for 30 cycles using reaction conditions that involved a denaturation step at 94° C. for 30 seconds, a primer annealing step at 65° C. for 30 seconds, and a primer extension step at 70° C. for 90 seconds using the following oligonucleotides: 5'-CTG TAC TGT GTA GTT AGA GAA AAT GGC-3' (SEQ ID NO: 5); and 5'-TTT TTA CGA GTG GTA ATG AAA ATA CAC GTG-3' (SEQ ID NO: 6).

Next, a 1:100 dilution of the first reaction product was used for conducting the subsequent nested PCR reaction. The nested PCR reaction was carried out for a total of 45 cycles using a denaturation step at 95° C. for 30 seconds, a primer annealing step at 58° C. for one minute, and primer extension step at 72° C. for one minute using the following oligonucleotides: 5'-CTG TAC TGT GTA GTT AGA GAA AAT GGC-3' (SEQ ID NO: 5); and 5'-Biotin-CCA CAC AAC TTT CTT TCT TGC TAG TG-3' (SEQ ID NO: 7). The resultant amplified PCR reaction product was analyzed using 1% agarose gel electrophoresis (Bio-Rad™) and visualized by ethidium bromide staining. The determination of the genetic variance of the BCHE gene was then completed using DNA sequencing.

The DNA sequencing of the BCHE-K polymorphism was conducted using an automated DNA sequencer (ALFexpress™ by Amersham Pharmacia Biotech) according to the manufacturers instructions and using the following sequencing primer: 5'-CY5-GCC-TTT-TGT-ATT-CGA-AAT-TAT-TTT-TC-3' (SEQ ID NO: 8).

In addition to BCHE genotyping, we performed apoE genotyping as follows. Allele-specific primer extension of purified brain DNA using a modification of the method of Main et al. was employed using primers labeled D, E, F, G, and H (synthesized by Genosys Biotech (The Woodlands, Tex.)) comprising sequence provided in Main et al. (Main R. F. et al., *J Lipid. Res.*, 32:183–187 (1991)). Reactions were carried out in a volume of 50 µL containing 1 µg of DNA; deoxyadenosine triphosphate, deoxycytidine triphosphate, deoxythymidine triphosphate and deoxyguanosine triphosphate, each 0.2 mmol/L; 10% dimethyl sulfoxide; 12.5 pmol of either primer D, E, F, or G; 25 pmol of primer H; and 10 µL of 10× PCR reaction buffer (Vector Biosystem, Toronto, ONT.). The DNA in the reaction mixture was first denatured for 10 min. at 96° C. and then cooled to 4° C. One unit of Taq polymerase (Vector Biosystem, Toronto, ONT.) was then added to each sample. Each sample was reheated for 2 min. at 96° C. and subjected to 30 cycles in a thermal cycler with each cycle consisting of a 10 sec. denaturation at 96° C., 30 sec. annealing at 58° C., and 1 min. extension at 65° C. The reaction products were visualized using 1% agarose gel electrophoresis and ethidium bromide. The gels were then photographed and the banding profile was compared to known standards.

In addition to the above-mentioned methods, the methods provided in any of the pending applications (U. S. Pat. Nos. 5,935,781 and 6,022,683, and U. S. Application Ser. Nos. 97/22699, 08/991,850, and 09/160,462) and following references (Brindle N. et al., *Hum. Mol. Genet.* 7:933–935 (1998); Singleton et al., *Hum Mol Genet* 7:937–939 (1998); Lehmann et al., *Hum. Mol. Genet.* 6:1933–1936 (1997); Richard et al., *Lancet* 349:539 (1997); and Gustincich S, et al., *Biotechniques* 11(3):298–300 (1998)) may also be used.

EXAMPLE 2

Use of the BCHE-K Allele as a Predictor of Non-Cholinomimetic Drug Efficacy

To demonstrate the effectiveness of the BCHE-K allele as a predictor of non-cholinomimetic drug efficacy in patients at risk for a neurological disease, we analyzed the genomic DNA and cognitive scores of the AD patient group of Richard et al. (*Lancet* 349:539 (1997)). In this study, 199 patients diagnosed with Alzheimer's disease were divided into two groups and one group (n=91) was administered a non-cholinomimetic therapy (the vasopressinergic drug, S12024, from Servier; administered at 100 mg per day) and the other group (n=108) was administered a placebo.

To quantitate changes in cognitive function during the clinical trial, patients were evaluated using the Mini Mental State Examination (MMSE) and a baseline score was determined for each patient prior to treatment. Following 12 weeks of drug or placebo treatment, both patient groups were re-evaluated using the same test. The difference in MMSE score results, before and after treatment, was determined for each patient in the study with a positive change in score indicating an improvement in cognitive ability and a negative change in score indicating a deterioration.

Butyrylcholinesterase genotyping was done as described in Example 1 and each patient was categorized as either possessing at least one BCHE-K allele (k-allele) or lacking the k-allele. That is, patients were dichotomized as either k-allele or non-k-allele subjects and the predictive value of the k-allele on the response to drug as measured by a difference in MMSE score results was used to determine its pharmacogenetic influence.

When the total number of patients administered a placebo (n=108) versus the total number of patients administered the non-cholinomimetic therapy S12024 (n=91), were analyzed for an improvement in their MMSE score irrespective of their k-allele genotype, no statistically significant difference was observed between the two groups (p>0.05). Analyzed in this way, the data would suggest that the non-cholinomimetic vasopressinergic therapy was ineffective for improving Alzheimer's disease in these patients (Table 1).

However, when the treated group was stratified using the k-allele genotype, a statistically significant difference (p<0.05) in drug-mediated improvement was observed in the non-k-allele subgroup (n=30) as compared to the k-allele subgroup (n=61) (Table 2). The non-k-allele group had the highest MMSE score, indicating an improvement in cognitive ability, while the k-allele group had the lowest MMSE score, indicating a deterioration in cognitive ability. Thus, the k-allele genotyping distinguished two genetically different groups within the treatment group that responded differently to non-cholinomimetic therapy. Stated another way, the k-allele genotyping revealed that there was indeed a patient subgroup that can favorably respond to the non-cholinomimetic therapy S12024 for AD.

Sorting placebo treated patients by k-allele genotype did not resolve a statistically significant difference (p>0.05) between the k-allele subgroup (n=69) and the non-k-allele subgroup (n=39) (Table 1).

TABLE 1

Absence of BCHE Correlated Improvement (as measured by MMSE) in Patients Treated with a Placebo

|  | mean | median |
| --- | --- | --- |
| total | −0.9 | −1.0 |
| non-k-allele | −1.1 | −1.0 |
| k-allele | −0.6 | −1.0 |

TABLE 2

BCHE Correlated Improvement (as measured by MMSE) in Patients Treated with a Non-Cholinomimetic Drug

|  | mean | median |
| --- | --- | --- |
| total | −0.1 | 0.0 |
| non-k-allele | +0.3 | 0.0 |
| K-allele | −1.0 | −1.5 |

EXAMPLE 3

Dual BCHE-K, ApoE4 Genotyping to Predict Non-Cholinomimetic Drug Efficacy

Having determined that the cognitive ability of members of the non-k-allele AD subgroup would be predicted to improve when administered a vasopressinergic drug, we wanted to determine if other markers associated with AD, alone or in combination with BCHE, had a predictive value with this drug.

We further analyzed the AD patient scores and genotyping analysis of Richard et al. (*Lancet* 349:539 (1997)) supplemented with additional butyrylcholinesterase k-allele genotyping as provided herein. For our analysis, we evaluated patients using two tests, the MMSE and ADAS-Cog, which quantitate changes in cognitive function. For changes in MMSE results, we considered a score of zero or larger as a positive response and for a difference in ADAS-Cog results, we considered a score of zero or lower a positive response. Thus, each AD patient was categorized as either having a response or non-response to drug treatment.

First, we analyzed the relationship between an AD patient's response to a non-cholinomimetic therapy (S12024 from Servier; administered at a dose of 100 mg per day) as a function of apoE4 genotype and these results are presented in Table 3.

TABLE 3

Number of Patients Responding to Non-Cholinomimetic Drug Treatment as a Function of ApoE Genotype

|  | Response | Non-response |
| --- | --- | --- |
| E4 | 40 | 23 |
| Non-E4 | 15 | 13 |

Chi square (Yate's correction) = 0.437 (p > 0.5)
Odds ratio = 1.51

Our analysis showed that AD patients with an apoE4 allele, who are given a non-cholinomimetic therapy are only 1.5 times more likely to respond to therapy than non-apoE4 AD patients and this difference is not statistically significant. Thus, we concluded that the apoE4 genotype alone does not influence the response of AD patients to a non-cholinomimetic therapy.

Next, we analyzed AD patients responding to a placebo as a function of their apoE4 genotype (Table 4). Our results showed that an AD patient's apoE4 genotype does not influence their response to a placebo.

TABLE 4

Number of Patients Responding to
Placebo Treatment as a Function of ApoE Genotype

|  | Response | Non-response |
|---|---|---|
| E4 | 29 | 37 |
| Non-E4 | 20 | 22 |

Chi square (Yate's correction) = 0.031 (p > 0.8)
Odds ratio = 0.86

By contrast, when we genotyped AD patients responding to a non-cholinomimetic vasopressinergic therapy for Alzheimer's disease, the absence of the k-allele was found to be a statistically significant predictor of a favorable drug response in the patient. Stated another way, the odds are that if a patient does not have a k-allele and is given the drug, they are three times more likely to respond to the drug than control patients having a k-allele (Table 5).

TABLE 5

Number of Patients Responding to Non-Cholinomimetic
Drug Treatment as a Function of BCHE Genotype

|  | Response | Non-response |
|---|---|---|
| Non-k allele | 42 | 19 |
| k-allele | 13 | 17 |

Chi square (Yates correction) = 4.46 (p < 0.035)
Odds ratio = 2.89

When a similar analysis was performed on patients responding or not responding to placebo as a function of their k-allele, no statistically significant correlation was observed (Table 6).

TABLE 6

Number of Patients Responding to Placebo
as a Function of BCHE Genotype

|  | Response | Non-response |
|---|---|---|
| Non-k allele | 34 | 35 |
| k-allele | 15 | 24 |

Chi square (Yates correction) = 0.78 (p > 0.35)
Odds ratio = 1.55

To summarize the predictive value of BCHE-K genotyping for determining the probability of a patient responding to therapy, the odds ratio of these data were calculated. The odds ratio of a patient with Alzheimer's disease responding to a non-cholinomimetic drug and having a non-k allele genotype is three fold over a k-allele matched control (Table 7).

TABLE 7

Summary of Odds Ratio for a Patient Response to Drug
as a Function of ApoE4 vs. BCHE

|  | placebo | treated |
|---|---|---|
| E4 | p > 0.8 O.R. = 0.86 | P > 0.5 O.R. = 1.51 |
| Non k-allele | p > 0.35 O.R. = 1.53 | P < 0.035 O.R. = 2.89 |

Similarly, AD patients who are apoE4 carriers and k-allele negative, are almost three times more likely to respond positively to a non-cholinomimetic therapy than a k-allele carrier (Tables 8 and 9).

TABLE 8

Number of Patients Responding to Drug as a Function of
Having a ApoE4 and BCHE Genotype

|  | responder | non-responders |
|---|---|---|
| E4 positive and k minus | 33 | 12 |
| all others | 22 | 24 |

Chi square (Yate's correction) = 5.2 (p < 0.025)
Odds ratio = 3

TABLE 9

Number of BCHE k Minus Patients Responding to Drug

|  | responder | non-responder |
|---|---|---|
| treated | 42 | 19 |
| placebo | 34 | 35 |

Chi square (Yate's correction) = 4.33 (p < 0.04)
Odds ratio = 2.28

EXAMPLE 4

Use of the BCHE-K Allele as a Predictor of Cholinomimetic Drug Efficacy

In order to demonstrate that the BCHE-K allele is predictive of patient response to other drugs outside the non-cholinomimetic drug class, we BCHE-genotyped AD patients being treated with the cholinomimetic drug tacrine.

We followed patients for 30 weeks of treatment with the cholinomimetic drug tacrine (Cognex® from Parke-Davis) using the MMSE test to quantitate changes in cognitive function. After 30 weeks of cholinomimetic drug treatment, the patient's MMSE score was compared to the patient's baseline MMSE score. We considered a patient with a positive MMSE value change as having a favorable response to the drug, and a patient having a zero or negative MMSE value change as not responding to the drug.

In Table 10, we present the number of patients responding or not responding to the cholinomimetic drug, tacrine, as a function of their BCHE-K genotype (see also FIG. 5). We observed that the number of non-k-allele patients responding positively to tacrine was three-fold higher than the number of non-k-allele positive patients who did not respond to tacrine. In the k-allele carrier group we observed virtually the same number of patients responding to drug as compared to patients not responding to drug.

TABLE 10

Number of Patients Responding to Tacrine as a
Function of Having a BCHE Genotype

|  | Responders | Non-responders |
|---|---|---|
| Non K-allele | 23 | 8 |
| K-allele | 10 | 7 |

To further determine how robust the BCHE-K polymorphism is as a predictor of a patient's treatment response, we calculated the odds ratio of being a responder with a non-k-allele. An odds ratio of 2.01 was calculated when taking the k-allele carrier status into account. Thus, we concluded that non-k-allele patients had a two-fold higher probability of responding well to a cholinomimetic therapy than k-allele patients. This conclusion is similar to the one we reached for non-k-allele patients administered a non-cholinomimetic vasopressinergic therapy (Examples 2 and 3).

EXAMPLE 5

Use of the BCHE-K and ApoE4 Allele to Determine a Patient's Risk for Alzheimer's Disease We have discovered that the combination of an apoE4 and BCHE-K allele contributes to define an individual's risk for the development of AD especially in patients between the ages of 60 and 75. To reach this conclusion, we compiled the apoE4 and BCHE-K genotypes for 224 AD patients and 97 age-matched healthy controls (Table 11) and analyzed the allelic frequency of these two genes in control patients versus patients with AD.

over represented only in AD patients. In this patient group, 48% of the AD patients had both alleles as compared to 16% of the healthy age-matched controls (Table 13).

TABLE 13

Frequency of BCHE-K and ApoE4 Allele Both Occurring in Controls vs. AD Patients

| Subjects | controls | cases | P (chi square Yates corr.) |
|---|---|---|---|
| All >60 years | 3/70 (4%) | 39/135 (29%) | <0.0001 |
| All >75 years | 1/27 (4%) | 28/89 (31%) | <0.008 |
| Apo E4 carrier > 60 years | 3/19 (16%) | 39/81 (48%) | 0.021 |
| Apo E4 carrier > 75 years | 1/9 (11%) | 28/54 (52%) | 0.056* |

*not significant

TABLE 11

Combined ApoE and BCHE Genotype Distribution

| | BCHE genotype | | | | | | | | | | | |
|---|---|---|---|---|---|---|---|---|---|---|---|---|
| | wt | | | | K-heterozygous | | | | K-homozygous | | | |
| APOE | AD | | Control | | AD | | Control | | AD | | Control | | Total | |
| Alleles | n | % | n | % | n | % | n | % | n | % | n | % | AD | Control |
| 2/2 | 0 (0) | 0.00 | 0 (0) | 0.00 | 0 (0) | 0.00 | 0 (0) | 0.00 | 0 (0) | 0.00 | 0 (0) | 0.00 | 0 (0) | 0 (0) |
| 2/3 | 3 (2) | 0.75 | 3 (1) | 0.50 | 0 (0) | 0.00 | 3 (0) | 0.50 | 1 (0) | 0.25 | 0 (0) | 0.00 | 4 (2) | 6 (1) |
| 2/4 | 2 (1) | 0.29 | 2 (1) | 1.00 | 5 (3) | 0.71 | 0 (0) | 0.00 | 0 (0) | 0.00 | 0 (0) | 0.00 | 7 (4) | 2 (1) |
| 3/3 | 35 (22) | 0.70 | 34 (14) | 0.76 | 12 (8) | 0.24 | 10 (2) | 0.22 | 3 (3) | 0.06 | 1 (1) | 0.02 | 50 (33) | 45 (17) |
| 3/4 | 32 (20) | 0.52 | 14 (7) | 0.82 | 25 (19) | 0.41 | 3 (1) | 0.18 | 4 (3) | 0.06 | 0 (0) | 0.00 | 61 (42) | 17 (8) |
| 4/4 | 8 (5) | 0.62 | 0 (0) | 0.00 | 5 (3) | 0.38 | 0 (0) | 0.00 | 0 (0) | 0.00 | 0 (0) | 0.00 | 13 (8) | 0 (0) |
| Total | 80 (50) | | 53 (23) | | 47 (33) | | 16 (3) | | 8 (6) | | 1 (1) | | 135 (89) | 70 (27) |

When we calculated the allelic frequency of the apoE4 or BCHE-K allele in controls and patients with AD, we found that the BCHE-K allelic frequency in AD cases was 23% as compared to 13% in healthy age-matched controls (Controls A, Table 12). Similarly, the apoE4 allelic frequency was higher in patients with AD (35%) as compared to age-matched controls (14%). For comparison, the apoE4 and BCHE-k allele frequency is provided for two other neurological diseases: multiple sclerosis (MS) and Parkinson's disease (PD).

TABLE 12

BCHE-K and Apo E4 Allele Frequencies in Study Group

| | No. Of subjects | F:M ratio | Mean age (SD) | BCHE-K allele frequency | Apo E4 allele frequency |
|---|---|---|---|---|---|
| Controls (A) >60 years | 70 | 0.56 | 74 (9.2) | 0.13 | 0.14 |
| Controls (B) >60 years | 64 | F only | 72 (10.2) | 0.20 | 0.12 |
| AD cases >60 years | 135 | 1.14 | 78 (7.8) | 0.23* | 0.35** |
| PD cases | 59 | F only | | 0.20 | 0.11 |
| MS cases | 64 | F only | | 0.16 | 0.12 |

*P < 0.02 chi-square Yate's corr. (vs Controls A)
**P < 0.0001 chi-square Yate's corr. (vs Controls A)

When we looked at the frequency of AD patients having both a BCHE-K allele and an apoE4 allele, as compared to age-matched controls, we observed that these alleles were A similar conclusion can be drawn from an analysis of the odds ratios calculated for AD patients and age-matched controls as a function of being apoE4 carriers. In this comparison, the probability of a confirmed AD patient with a BCHE-K allele also having an apoE4 allele is two-fold higher over age-matched controls (Table 14).

Conversely, when these data are analyzed by calculating the odds ratio of a confirmed patient with an apoE4 allele as also having a BCHE-K allele, the odds are over two-fold higher compared to age-matched controls (Table 15).

TABLE 14

Odds Ratios of Confirmed AD for BCHE-K Alleles

| Subjects | Cases | Controls | Odds ratio (alleles) | 95% C.I. | Odds ratio (carriers) | 95% C.I. |
|---|---|---|---|---|---|---|
| All >60 years | 135 | 70 | 2.1 | 1.15–3.85 | 2.1 | 1.1–4.1 |
| All >75 years | 89 | 27 | 3.3 | 1.2–9.1 | 4.5 | 1.4–15 |
| Apo E4 carriers > 60 years | 81 | 19 | 4.2 | 1.2–15 | 4.95 | 1.3–19 |
| Apo E4 carriers > 75 years | 54 | 9 | 6.8* | 0.8–55 | 8.6* | 0.95–79 |

*not significant

TABLE 15

Odds Ratios of Confirmed AD for Apo E4 Alleles

| Subjects | Cases | Con-trols | Odds ratio (alleles) | 95% C.I. | Odds ratio (carriers) | 95% C.I. |
|---|---|---|---|---|---|---|
| All >60 years | 135 | 70 | 3.4 | 2.0–5.8 | 4.0 | 2.1–7.5 |
| All >75 years | 89 | 27 | 2.7 | 1.2–6.1 | 3.1 | 1.2–8.2 |
| BCHE-K carriers > 60 years | 55 | 17 | 6.9 | 2.1–23 | 11.4 | 3.0–43 |
| BCHE-K carriers > 75 years | 39 | 4 | 4.6* | 0.3–64 | 7.6* | 0.4–147 |

*not significant

In Table 16, we provide the odds ratios for AD subjects carrying at least one allele of apoE4 and BCHE-K as compared to control subjects who have neither allele. In subjects between 60 and 75 years of age who carry both an apoE4 and BCHE-K alleles, the odds ratio of having AD is 12.7 fold higher than age-matched controls. For subjects greater than 75 years of age, the odds ratio of having AD is 17.5 fold higher than age-matched controls. These data predict a strong correlation between the presence of these two alleles and being at risk for AD.

TABLE 16

Odds ratios of confirmed AD for BCHE-K alleles

| Apo E4 carriers | BCHE-K carriers | Controls | Cases | Odds ratio | 95% C.I. |
|---|---|---|---|---|---|
| All >60 years | | | | | |
| − | − | 37 | 38 | Reference | |
| − | + | 14 | 16 | 1.1 | not significant |
| + | − | 16 | 42 | 2.6 | 1.2–5.8 |
| + | + | 3 | 39 | 12.7 | 4.1–39 |
| All >75 years | | | | | |
| − | − | 15 | 24 | Reference | |
| − | + | 3 | 11 | 2.3 | not significant |
| + | − | 8 | 26 | 2.0 | not sign. (0.6–6.7) |
| + | + | 1 | 28 | 17.5 | 2.8–108 |

In summary, we have discovered that determining an individual's apoE4 and BCHE-K allele status is a useful tool in the prediction of an individual's risk for AD. Furthermore, our results demonstrate that prognostic forecasting can afford patients the ability to start prophylactic therapies before disease strikes. For example, the risk of AD can be calculated for asymptomatic, healthy individuals as young adults and well before the onset of measurable symptoms. Then, as the individual ages, preventive therapies can be invoked in order to prevent or lessen the progression of AD later in life.

Other Embodiments

The invention described herein provides a method for treating patients with a neurological disease risk by determining the patients' BCHE-K allele status and providing a forecast of the patients' ability to respond to a given drug treatment. In particular, the invention provides a method for determining, based on the presence or absence of the BCHE-K polymorphism, a patient's likely response to two major classes of drug therapies used in the treatment of neurological diseases (i.e., cholinomimetic and non-cholinomimetic). We conclude that, given the predictive value of the BCHE-K polymorphism across two different classes of drug, having different mechanisms of action, the BCHE-K polymorphism is likely to have a similar predictive value for other drugs acting through other pharmacological mechanisms. Thus, the methods of the invention may be used to determine a patient's response to other drugs including, without limitation, monoamine oxidase inhibitors, muscarinic agonists, neurotrophic factors, noradrenergic factors, antioxidants, and anti-inflammatories.

In addition, while determining the presence or absence of the butyrylcholinesterase K allele is a clear predictor for determining the efficacy of a drug in a given patient, other BCHE allelic variants of reduced catalytic activity are envisioned as predicting drug efficacy using the methods described herein. In particular, the methods of the invention may be used to treat patients with any of the following known BCHE mutations (e.g., deletions (BCHE*FS4), missense mutations (BCHE*24 M, *1005, *250P, *267R, *330I, *365R, *418S, *515C), and nonsense mutations (BCHE*119STOP, *465STOP)).

In addition, while the methods described herein are preferably used for the treatment of human patients, non-human animals (e.g., pets and livestock) may also be treated using the methods of the invention.

All publications and patent applications mentioned in this specification are herein incorporated by reference to the same extent as if each independent publication or patent application was specifically and individually indicated to be incorporated by reference.

Other embodiments are within the claims.

What is claimed is:

1. A method for treating a patient at risk for or diagnosed with Alzheimer's disease, said method comprising
determining the genotype at nucleotide 1828 of the BCHE gene of said patient and predicting the efficacy of a therapy for treating said patient,
wherein the detection of an adenine at position 1828 indicates a predisposition to non-responsiveness to cholinomimetic or vasopressinergic therapy and the detection of guanine homozygosity at position 1828 indicates a predisposition to responsiveness to cholinomimetic or vasopressinergic therapy, and
wherein said therapy comprises administering a cholinomimetic or vasopressinergic therapy to patients having guanine homozygosity at position 1828 of the BCHE gene.

2. A method for selecting cholinomimetic or vasopressinergic therapy for a patient at risk for or diagnosed with Alzheimer's disease, said method comprising determining the genotype at nucleotide 1828 of the BCHE gene of said patient, wherein the detection of an adenine at position 1828 indicates a predisposition to non-responsiveness to cholinomimetic or vasopressinergic therapy and the detection of guanine homozygosity at position 1828 indicates a predisposition to responsiveness to cholinomimetic or vasopressinergic therapy, said genotype indicating whether said cholinomimetic or vasopressinergic therapy is a suitable therapy for said patient.

3. A method for stratifying a patient in a subgroup of a clinical trial of a cholinomimetic or vasopressinergic therapy for the treatment of Alzheimer's disease, said method comprising determining the genotype at nucleotide 1828 of the BCHE gene of said patient, wherein the detection of an adenine at position 1828 indicates a predisposition to non-responsiveness to cholinomimetic or vasopressinergic therapy and the detection of guanine homozygosity at position 1828 indicates a predisposition to responsiveness to cholinomimetic or vasopressinergic therapy, and wherein said genotype enables the stratification of said patient into a subgroup for said clinical trial.

4. The method of claim 1, 2, or 3, wherein said therapy is a cholinomimetic drug.

5. The method of claim 4, wherein said drug is tacrine.

6. The method of claim 1, 2, or 3, wherein said therapy is a vasopressinergic drug.

7. The method of claim 1, 2, or 3, wherein said therapy further comprises probucol, a monoamine oxidase inhibitor, muscarinic agonist, neurotrophic factor, noradrenergic factor, antioxidant, anti-inflammatory, corticotrophin-releasing hormone (CRH), somatostatin, substance P, neuropeptide Y, or thyrotrophin-releasing hormone (TRH).

8. A method for treating a patient at risk for or diagnosed with Alzheimer's disease, said method comprising:
a) determining the genotype at nucleotide 1828 of the BCHE gene of said patient, wherein the detection of an adenine at position 1828 indicates a predisposition to non-responsiveness to cholinomimetic or vasopressinergic therapy and the detection of guanine homozygosity at position 1828 indicates a predisposition to responsiveness to cholinomimetic or vasopressinergic therapy;
b) determining the presence or absence of an apoE4 allele in said patient; and
c) administering a cholinomimetic or vasopressinergic therapy to patients having guanine homozygosity at position 1828 of the BCHE gene and having an apoE4 allele.

* * * * *

UNITED STATES PATENT AND TRADEMARK OFFICE
CERTIFICATE OF CORRECTION

PATENT NO.    : 6,291,175 B1
DATED         : September 18, 2001
INVENTOR(S)   : Pierre Sévigny et al.

It is certified that error appears in the above-identified patent and that said Letters Patent is hereby corrected as shown below:

<u>Title page,</u>
Item [75], Inventors, replace "Amouye" with -- Amouyel --;
Item [56], Crawford et al, replace "indepetdently" with -- independently --;

<u>Column 3,</u>
Line 13, replace "Gamier" with -- Garnier --;

<u>Column 6,</u>
Line 45, replace "J Lipid. Res." with -- J. Lipid. Res. --;
Lines 66 to 67, replace "U.S. Application Ser. Nos. 97/22699" with -- U.S. Application Nos. U.S. 97/22699 --.

Signed and Sealed this

Sixth Day of August, 2002

Attest:

Attesting Officer

JAMES E. ROGAN
*Director of the United States Patent and Trademark Office*